US008771655B2

(12) United States Patent
Marino

(10) Patent No.: US 8,771,655 B2
(45) Date of Patent: Jul. 8, 2014

(54) NATURAL NAIL POLISH

(76) Inventor: Debra Marino, Long Beach, NY (US)

(*) Notice: Subject to any disclaimer, the term of this patent is extended or adjusted under 35 U.S.C. 154(b) by 0 days.

(21) Appl. No.: 13/426,432

(22) Filed: Mar. 21, 2012

(65) Prior Publication Data

US 2012/0260932 A1 Oct. 18, 2012

Related U.S. Application Data

(60) Provisional application No. 61/476,031, filed on Apr. 15, 2011.

(51) Int. Cl.
*A61Q 3/02* (2006.01)

(52) U.S. Cl.
USPC .......................................................... 424/61

(58) Field of Classification Search
None
See application file for complete search history.

(56) References Cited

U.S. PATENT DOCUMENTS

| 5,120,529 A * | 6/1992 | Koch et al. ....................... 424/61 |
| 5,276,075 A * | 1/1994 | Santini ............................. 524/40 |
| 2007/0148111 A1* | 6/2007 | Simpson ......................... 424/63 |

OTHER PUBLICATIONS

The Painting Effects website entry for Medium or Glaze dated 2000; http://www.painting-effects.co.uk/mediums.htm.*
The Esprit Cabane website entry for Paint Recipe Q&A part 2 dated Jan. 2008; http://en.espritcabane.com/paint-recipes/paint-recipe-faq-part2.php.*
The Jun-blog entry "How to make red food coloring from red beet powder," dated Dec. 13, 2010: http://blog.junbelen.com/2010/12/13/how-to-make-red-food-coloring-from-red-beet-powder/.*

* cited by examiner

*Primary Examiner* — Ileana Popa
*Assistant Examiner* — Alissa Prosser
(74) *Attorney, Agent, or Firm* — Scully, Scott, Murphy & Presser, P.C.

(57) ABSTRACT

A natural nail polish composition made with all natural fruits and vegetable and only nontoxic ingredients. The natural nail polish composition comprises a lemon juice solution, a powdered form of fruits and/or vegetables, a powdered form of cane sugar, a nontoxic water soluble acrylic polymer, and a plurality of nontoxic colors. The plurality of colors comprises water soluble nontoxic pigments, nontoxic pigments, nontoxic mica, and nontoxic nail glitter. The natural nail polish composition is safe to use among young children because the composition is completely nontoxic. Since the composition is nontoxic, any kind of complications that may happen due to the chemicals in the traditional nail polish are completely prevented. The natural nail polish composition has a unique method of applying and removing the product. The natural nail polish composition can be mixed with the lacquer or shellac type products and creates an alternative nail polish composition.

12 Claims, 5 Drawing Sheets

NATURAL NAIL POLISH

The current application claims a priority to the U.S. Provisional Patent application Ser. No. 61/476,031 filed on Apr. 15, 2011.

FIELD OF THE INVENTION

The present invention relates generally to a composition of nail polish. More particularly, the present invention is an all natural nail polish which is made by using fruits and vegetables, nontoxic pigments and/or nontoxic premade water soluble pigments and/or nontoxic mica, providing a healthier and more environmentally friendly nail polish solution designed for, but not limited to, girls of ages 3 years and up. However, the present invention is a water-soluble based nail polish but may also be mixed with shellac, lacquer, or other like substances if so desired, to add longevity.

BACKGROUND OF THE INVENTION

Nail polish formulas often use ingredients including, but not limited to, phthalates, toluene, and formaldehyde, all of which are toxic materials. Currently, many nail polish producing companies are trying to reduce these toxins because of their toxic properties and the detrimental long-term consequences following regular usage of these ingredients. It is therefore an object of the present invention to introduce a nail polish composition which reduces and minimizes the common use of toxic materials and replacing them with all-natural fruits and vegetables and nontoxic ingredients.

DETAIL DESCRIPTIONS OF THE INVENTION

All illustrations of the drawings are for the purpose of describing selected versions of the present invention and are not intended to limit the scope of the present invention.

The present invention, a natural nail polish, is composed of a natural nail polish composition and an alternative nail polish composition. The present invention is the only nail polish which comprises fruits and vegetables as ingredients in a water-based composition. The fruits and vegetables are also used for natural cosmetics and skin care creams which help with skin integrity while adding beauty without toxins to skin. The present invention is a quick drying, odorless, non-carcinogenic, and animal friendly product. The present invention does not require a top and/or bottom coat like traditional nail polishes. Because there is no top and/or bottom coat, the cleaning process of the present invention is much easier and can be done without using any kind of chemicals. The present invention does not contain formaldehyde, toluene, phthalates, bisphenol A, camphor, toxic pigments, toxic mica, synthetic metals, synthetic colors, any artificial dyes, and iron. The absence of the above harmful ingredients in the natural nail polish composition makes the present invention completely non-toxic and the natural nail polish composition safe among children. The natural nail polish composition is designed for all age groups starting from the age group of three. The alternative nail polish composition is also made by combining the natural nail polish composition with a top coat nail polish, lacquer, shellac, or any other related product. The downside of using top coat nail polish, lacquer, shellac, or any other related product is that the alternative nail polish composition becomes a toxic composition, which is not recommended for use with children.

Figure 1:
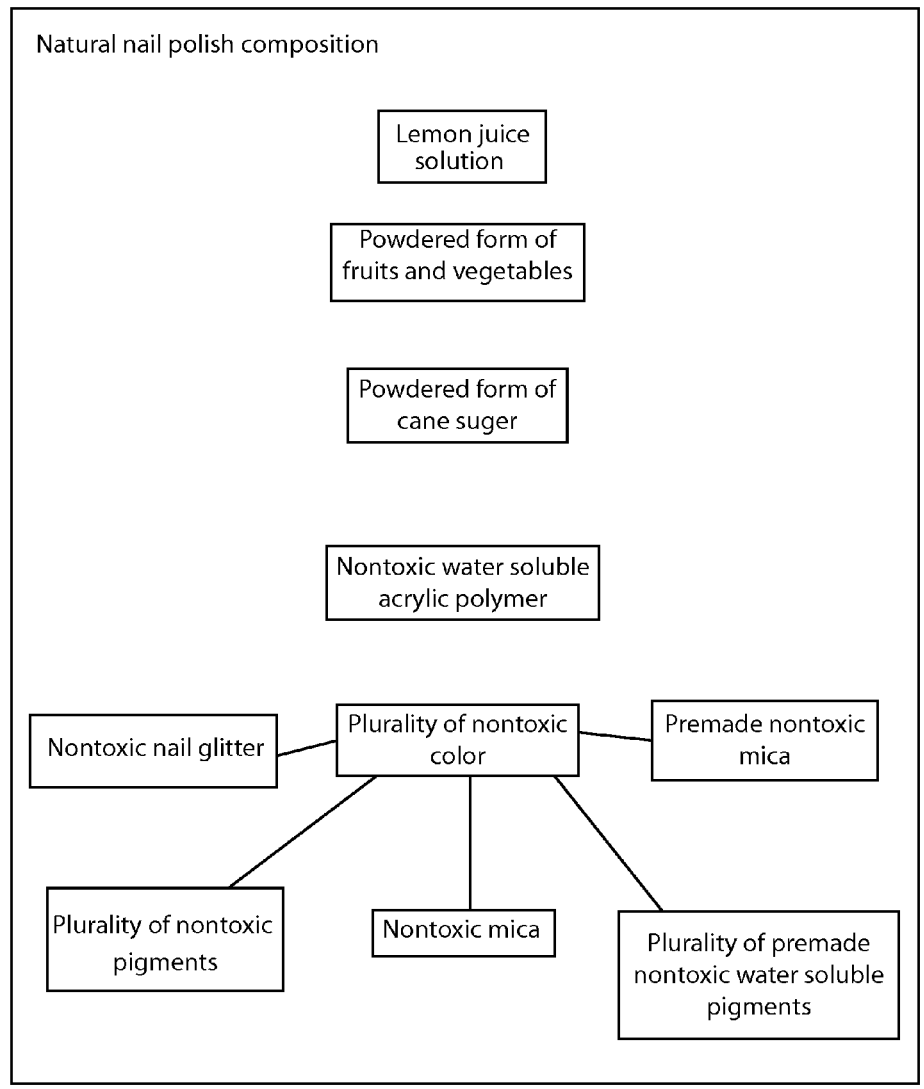
FIG. 1 is a view of the system for a natural nail polish composition.
Figure 3:
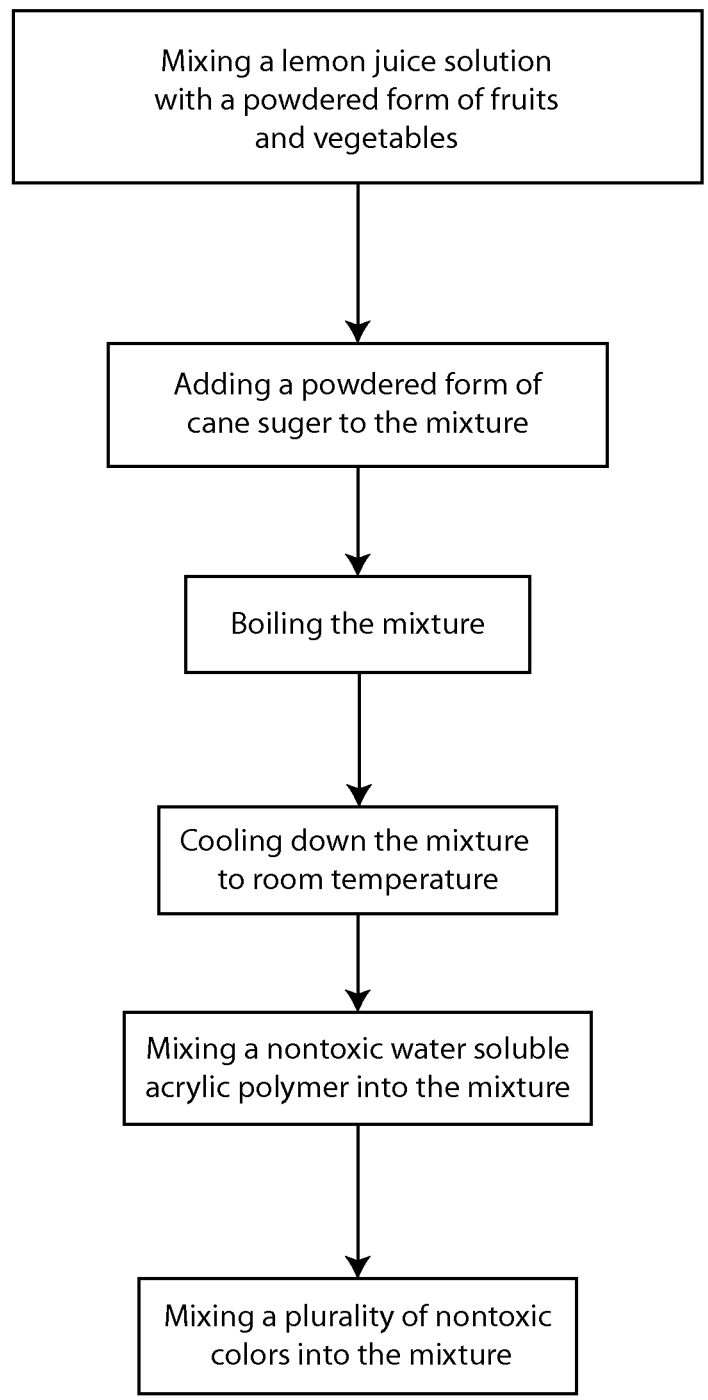
FIG. 3 is a flow chart illustrating the method of making the natural nail polish composition.

In reference to FIGS. 1 and 3, the natural nail polish composition comprises a lemon juice solution, a powdered form of fruits and/or vegetables, a powdered form of cane sugar, nontoxic water soluble acrylic polymer, and a plurality of nontoxic colors. The lemon juice solution used in the natural nail polish composition is similar to traditional pure lemon juice which is widely available in many retail stores. The lemon juice solution comprises lemon juice and filtered water. If lemon juice is concentrated, it may comprise sodium benzoate and lemon oil. The powdered form of cane sugar used in the natural nail polish composition is also similar to traditional powdered form of cane sugar which is available in many retail stores. A lemon mixture is formulated by mixing the lemon juice solution, the powdered form of fruits and/or vegetables, and cane sugar. The lemon mixture comprises 70 to 75 percent of the lemon juice solution with 20 to 30 percent of the powdered form of fruits and/or vegetables and 1 to 3 percent of the powdered form of cane sugar.

Ratio of the powdered form of fruits and/or vegetables determines the expected color of the natural nail polish composition. Different kinds of powdered form of fruits and/or vegetables also determine the different colors in the natural nail polish composition. The powdered form of fruits and/or vegetables may contain one or more of the following: red beet, carrot, acerola berry, broccoli, spinach, kale, spirulina, acai, blueberry, blackberry, black currant, elderberry, passion fruit, goji, pomegranate, strawberry and many more types of fruits & vegetables. For example, if the intended color of the natural nail polish composition is red, then the powdered form of red beet is used. After the mixing process is finished, the lemon mixture is boiled and cooled down to room temperature. After the lemon mixture reaches the room temperature, 8 to 18 percent of the lemon mixture is then added to the nontoxic water soluble acrylic polymer and mixed thoroughly. The natural nail polish composition comprises 70 to 80 percent of nontoxic water soluble acrylic polymer.

If the lemon mixture is not used after it reaches room temperature, the lemon mixture needs to be placed in a refrigerator for future use. The refrigerated lemon mixture may last up to nine months to one year. The refrigerated lemon mixture has to be brought up to room temperature before it is used with other ingredients. In order to obtain certain colors and effects, the plurality of nontoxic colors is added to the lemon mixture and the nontoxic water soluble acrylic polymer mixture and mixed well. The lemon mixture and the nontoxic water soluble acrylic polymer mixture may or may not need to be strained before adding the plurality of nontoxic colors. The plurality of nontoxic colors comprises a plurality of premade nontoxic water soluble pigments, premade nontoxic mica, a plurality of nontoxic pigments, nontoxic mica, and nontoxic nail glitter. The natural nail polish composition comprises 10 to 20 percent of the plurality of premade nontoxic water soluble pigments or the plurality of nontoxic pigments, and/or 10 to 20 percent of the premade nontoxic mica or nontoxic mica, and/or 5 to 15 percent of the nontoxic nail glitter. Use of the plurality of nontoxic colors varies from one composition to another and one plurality of colors or combination of many plurality of color can be used during the mixing process. For example, a cream color natural nail polish composition can be made without using nontoxic nail glitter to accommodate a reduce brightness. After the correct natural nail polish composition has been achieved, the natural nail polish composition is put into bottles, which are hermetically sealed. The bottles are kept at room temperature for better shelf life and the bottles comprise a non-coated nail polish applying brush.

Since no toxic chemicals have been used in the natural nail polish composition, the traditional toxic smell which comes out from the traditional nail polish compositions is completely eliminated from the natural nail polish composition. The natural nail polish composition can be used by anyone as a healthy and safe alternative to traditional nail polishes because the natural nail polish composition prevents long term inhalation type diseases due to toxic chemicals. At the same time, consumers are able to have beautiful painted nails by using the natural nail polish composition which is also easy to apply. The natural nail polish composition can also be used by pregnant women, cancer survivors, and cancer patients because the natural nail polish composition is water-soluble and nontoxic. Due to the fact the natural nail polish composition is made from fruits and/or vegetables, anyone who has food allergies must avoid using the present invention because they might have allergic reactions due to some of the ingredients that have been used.

Figure 2:
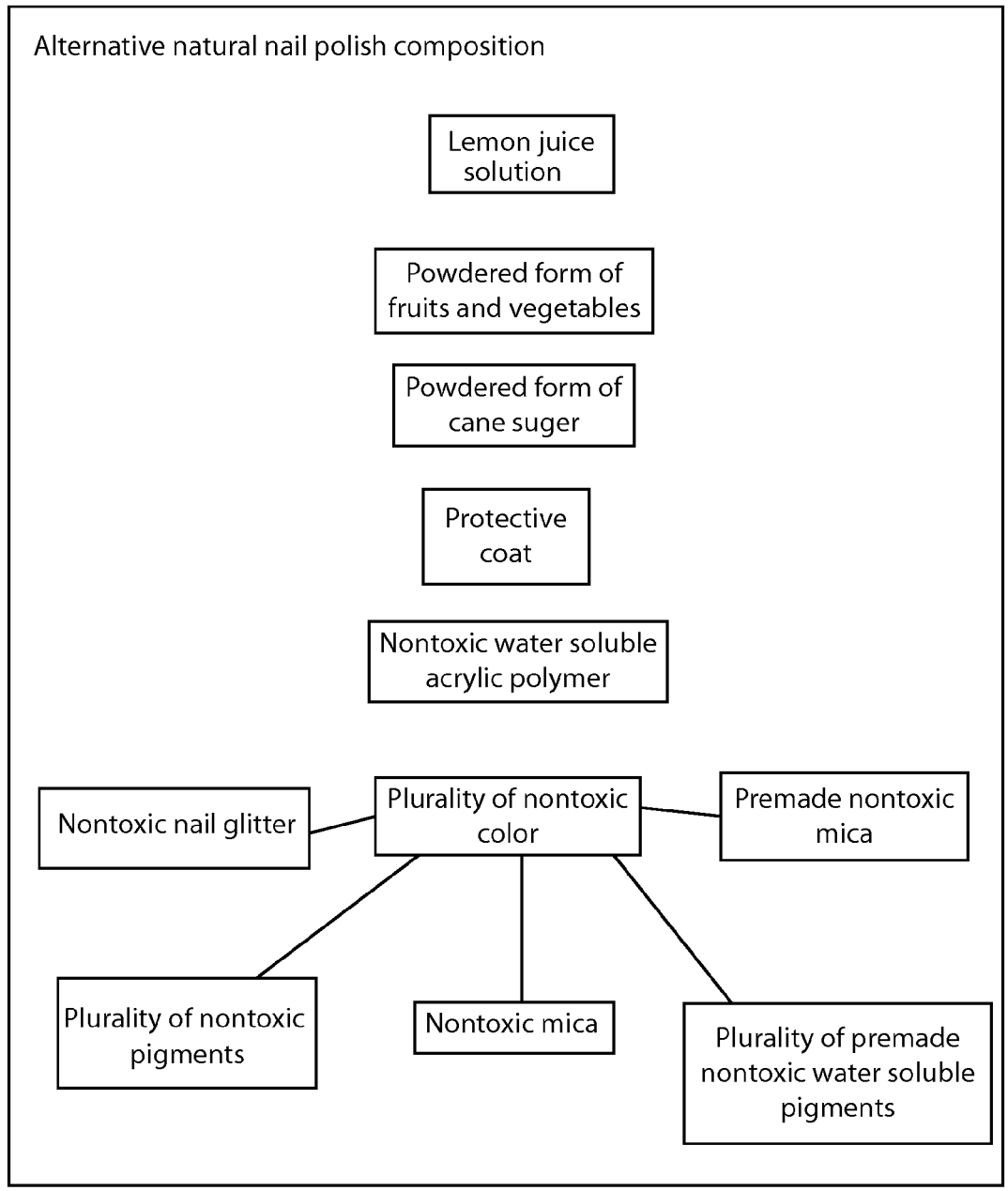
FIG. 2 is a view of the system for an alternative nail polish composition.
Figure 4:
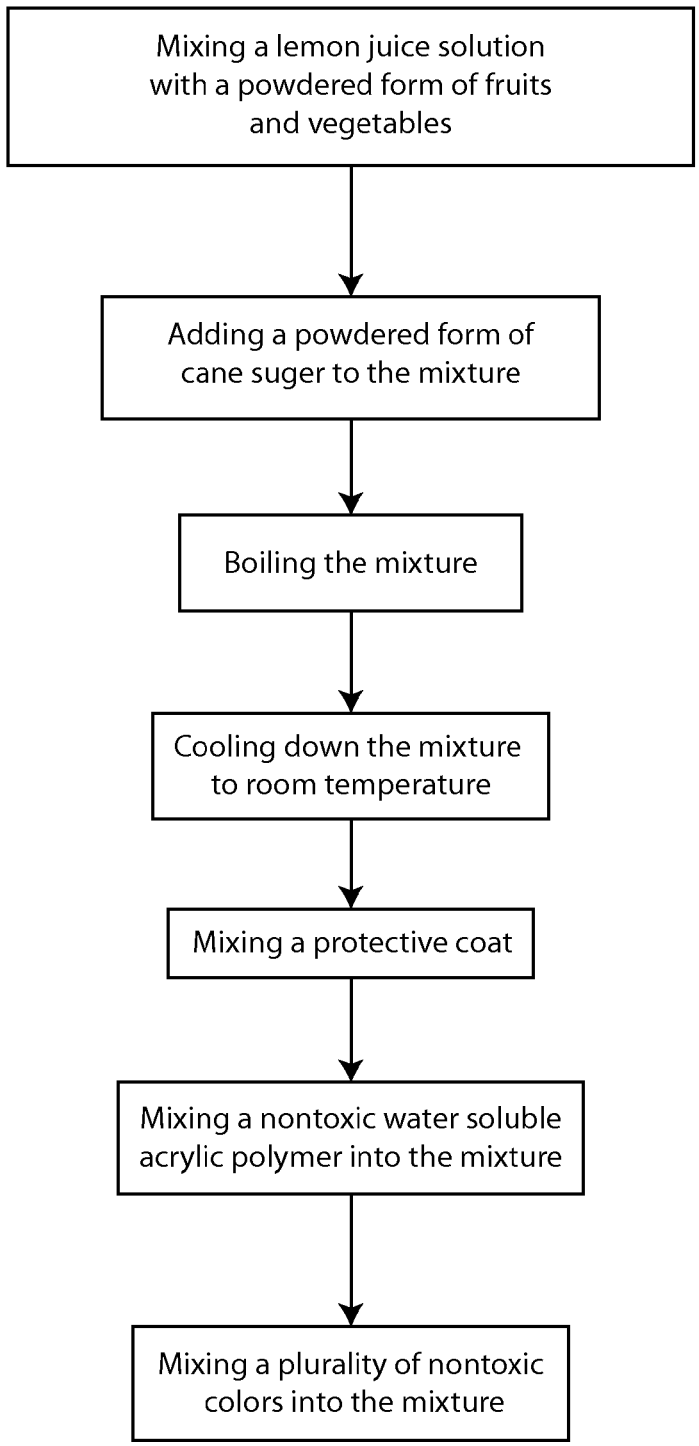
FIG. 4 is a flow chart illustrating the method of making the alternative nail polish composition.

In reference to FIGS. 2 and 4, the alternative nail polish composition comprises all of the ingredients from the natural nail polish composition and a protective coat. The protective coat may be a top coat nail polish solution, a lacquer solution, a shellac solution or any other related products. The addition of the protective coat increases the longevity of the natural nail polish composition and the protective coat prevents the users from having to apply a separate top coat and/or bottom coat as they do with the traditional nail polishes.

An alternative lemon mixture is formulated by mixing 70 to 75 percent of the lemon juice solution with 20 to 30 percent of powdered form of fruits and/or vegetables, and then 1 to 3 percent of the powdered form of cane sugar is added to the alternative lemon mixture. The ratio of the powdered form of fruits and/or vegetables determines the expected color of the alternative nail polish composition. Different kinds of powdered form of fruits and/or vegetables also determine the different colors in the alternative nail polish composition. The powdered form of fruits and/or vegetables may contain one or more of the followings: red beet, carrot, acerola berry, broccoli, spinach, kale, spirulina, acai, blueberry, blackberry, black currant, elderberry, passion fruit, goji, pomegranate, strawberry and many more types of fruits and/or vegetables. For example, if the intended color of the alternative nail polish composition is blue, powdered form of blueberry is used. After the mixing process is finished, the alternative lemon mixture is boiled and cooled down to room temperature. After the alternative lemon mixture reaches room temperature, 8 to 18 percent of the cooled down alternative lemon mixture is then thoroughly mixed with the 1 to 15 percent of the protective coat and then mixed into the nontoxic water soluble acrylic polymer. The alternative nail polish composition comprises 70 to 80 percent of nontoxic water soluble acrylic polymer so proper colors can be achieved in the alternative nail polish composition.

In order to obtain the desired color, the plurality of nontoxic colors is added to the alternative lemon mixture and nontoxic water soluble acrylic polymer mixture and mixed well. The alternative lemon mixture and nontoxic water soluble acrylic polymer mixture may or may not need to be strained before adding the plurality of nontoxic colors. The plurality of nontoxic colors comprises a plurality of premade nontoxic water soluble pigments, premade nontoxic mica, a plurality of nontoxic pigments, nontoxic mica, and nontoxic nail glitter.

Use of the plurality of nontoxic colors varies from one alternative nail polish composition to another. Each of the plurality of colors is independent from each other so one or many can be used during the mixing process. For example, the alternative nail polish composition can be made without using either the premade nontoxic mica or nontoxic mica. The alternative nail polish composition comprises 10 to 20 percent of the plurality of premade nontoxic water soluble pigments or nontoxic pigments and/or 10 to 20 percent of the premade nontoxic mica or nontoxic mica. If the nontoxic nail glitter is used in the alternative nail polish composition, the percentage ranges from 5 to 15. After the correct alternative nail polish composition has been achieved, the alternative nail polish composition is put into bottles, which are hermetically sealed. Bottled alternative nail polish composition is then kept at room temperature for better self life and the bottles comprise a non-coated nail polish applying brush. A coated mixing brush is used throughout the whole process of formulating the alternative nail polish composition. The alternative lemon mixture needs to be put in a refrigerator for future use if the alternative lemon mixture is not used immediately. The refrigerated alternative lemon mixture may last from nine months to one year.

Figure 5:
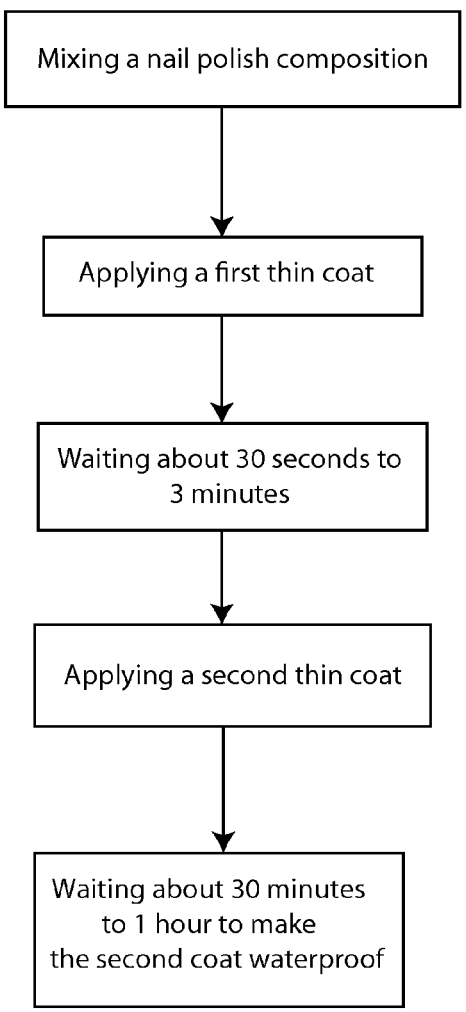
FIG. 5 is a flow chart illustrating the method of applying and removing process of the present invention.
Figure 5:
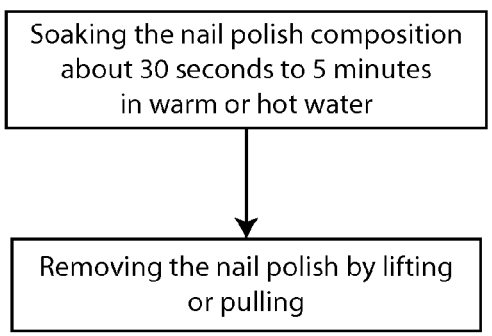

Applying process of the natural nail polish:

In reference to FIG. 5, the present invention is applied on a person's nails which can be natural nails or synthetic nails. The nails should be completely clean and dry before the present invention is applied. The present invention is shaken well within the bottle, before applying onto the nails and a first thin coat of the present invention is then applied onto the nails. The thickness of the first thin coat is smaller than the thickness of the traditional nail polish coat because of the ingredients in the present invention. The first thin coat must be dry before applying a second thin coat. Time required to dry the first thin coat depends on the thickness of the first thin coat. In average, the total time required to dry the first thin coat ranges from thirty seconds to three minutes. After the first thin coat is dry, the second thin coat is applied onto the nails. Time required to dry the second thin coat also depends on the thickness of the second thin coat. In average, total time required to dry the second thin coat ranges from thirty seconds to three minutes. After the second coat is added, in order for the natural nail polish to become water proof, the user must wait thirty minutes to one hour before getting the natural nail polish applied nails wet. If the present invention gets on the skin while being applied to the nails, then the excess natural nail polish composition or alternative nail polish composition should be wiped off with a clean cloth or tissue. If the natural nail polish composition or alternative nail polish composition on the skin is completely dry, then those dried compositions can be lightly and easily scratched off from the skin or removed with wet wash cloth or wet paper towel.

When the present invention is applied and dried correctly, it can last as long as commercial chemical nail polishes. The average lasting time of the present invention is about three days or more on fingernails and at least two weeks on the toenails. However, it is recommended that the present invention or any other kind of nail polishes should be removed after seven days for health purposes so that the nails can breathe.

Removing process of the natural nail polish:

Removal of the natural nail polish composition or alternative nail polish composition can be done with two different methods. In reference to FIG. 5, the first method, the nails are directly soaked in warm or hot water flowing from a shower or sink faucet, or the nails are directly soaked while taking a warm or hot water bath. In either case, a soaking time ranges from thirty seconds to five minutes. Depending on the water temperature, the soaking time may increase beyond five minutes. After the nails have been soaked in warm or hot water, the natural nail polish composition or alternative nail polish composition becomes softer. Then, the soft natural nail polish composition or alternative nail polish composition can be easily lifted up or pulled up like a sticker from the base of the nail cuticles, without damaging the nails. If the natural nail polish composition or alternative nail polish composition becomes soft and it is not desired to be removed, the nails should be immediately rinsed with a cold water flow for at least ten seconds. The cold water flow restores the original hardness of the present invention. As for the second method, the nails can be applied with natural nail polish removers and a clean cloth or tissue is used to wipe off the present invention.

If the hard natural nail polish composition or alternative nail polish composition is pulled, rubbed, or scraped off from the nails when the natural nail polish is hard, it may harm the nails. The present invention is designed to come off easily so that children can change colors as often as wanted. The natural nail polish composition or alternative nail polish composition also has the capability of staying for a long period of time as the commercial nail polishes. Since the present invention is water-soluble, the clean-up process is much easier. Using water or water and soap, wipes off wet or dry natural nail polish composition or alternative nail polish composition on most common kitchen, bathroom, and wood floors and on most daily worn common clothing. If the present invention has been dried for several days, common commercial cleaners can be used with or without a steel wool type pad. The present invention is not recommended to get on furniture, hand washable, or dry cleaning type of clothing or rugs.

As long as the present invention is kept in room temperature and inside the air sealed bottle, the shelf life of the present invention is very similar to commercial nail polishes. During storage the colors may separate causing different colored layers; this is the reason the present invention is mixed well before applying onto the nails. The composition used in the present invention is not made for consumption, only for application onto the nails. However, the natural nail polish (not including the alternative composition) is not harmful if ingested but not made to be ingested.

Although the invention has been explained in relation to its preferred embodiment, it is to be understood that many other possible modifications and variations can be made without departing from the spirit and scope of the invention as hereinafter claimed.

What is claimed is:
1. A natural nail polish consisting of:
(a) a lemon mixture; a lemon juice solution, a powdered form of fruits and/or vegetables, a powdered form of cane sugar,
(b) a nontoxic water soluble acrylic polymer; and
(c) one or more additional compounds selected from the group consisting of a plurality of nontoxic colors and a protective coat.

2. The natural nail polish as claimed in claim 1, wherein the lemon mixture is about 8% to about 18% by volume; the nontoxic water soluble acrylic polymer is about 70% to about 80% by volume; the plurality of nontoxic colors is about 10% to about 20% by volume; and the protective coat is about 1% to about 12% by volume of the protective coat.

3. The natural nail polish as claimed in claim 2, wherein the lemon mixture is about 70% to about 75% by volume of the lemon juice solution; about 1% to about 3% by volume of the powdered form of cane sugar; and about 20% to about 30% by volume of the powdered form of fruits and/or vegetables.

4. The natural nail polish as claimed in claim 2, wherein the plurality of nontoxic colors are selected from the group consisting of a plurality of premade nontoxic water soluble pigments, a plurality of nontoxic pigments, nontoxic mica, and a nontoxic nail glitter.

5. The natural nail polish as claimed in claim 2, wherein the protective coat is selected from the group consisting of a top coat nail polish solution, a lacquer solution, and a shellac solution.

6. The natural nail polish as claimed in claim 4, wherein the plurality of nontoxic colors are, out of 55 total parts by volume, about 10 to about 20 parts by volume of the plurality of premade nontoxic water soluble pigments; about 10 to about 20 parts by volume of the nontoxic mica; and about 5 to about 15 parts by volume of the nontoxic nail glitter.

7. The natural nail polish as claimed in claim 4, wherein the plurality of nontoxic colors are, out of 55 total parts by volume, about 10 to about 20 parts by volume of the plurality of nontoxic pigments; about 10 to about 20 parts by volume of the nontoxic mica; and about 5 to about 15 parts by volume of the nontoxic nail glitter.

8. A method of making a natural nail polish according to claim 1 comprising the steps of: (1) formulating a base mix by thoroughly mixing a lemon juice solution, and a powdered form of fruits and/or vegetables; (2) formulating a second mixture by adding a powdered form of cane sugar into the base mixture and mixed together; (3) boiling of the second mixture is performed by a heating source; (4) allowing the boiled second mixture to cool down into room temperature; (5) adding the second mixture into a nontoxic water soluble acrylic polymer, after the second mixture is cooled down into room temperature; (6) mixing the second mixture and the nontoxic water soluble acrylic polymer; and (7) mixing compounds selected from the group consisting of a protective coat and a plurality of nontoxic colors into the mixture.

9. The method of making the natural nail polish as claimed in claim 8 wherein, the plurality of nontoxic colors are selected from the group consisting of a plurality of premade nontoxic water soluble pigments, a plurality of nontoxic pigments, nontoxic mica, and a nontoxic nail glitter.

10. The method of making the natural nail polish as claimed in claim 8 wherein the protective coat is selected from the group consisting of a top coat polish solution, a lacquer solution, and a shellac solution.

11. A method of applying and removing a natural nail polish, comprising the steps of: (1) providing a plurality of nails, wherein the plurality of nails includes natural nails and synthetic nails; (2) providing the natural nail polish of claim 1, wherein the natural nail polish is located within a bottle; (3) thoroughly mixing the natural nail polish by shaking the bottle; (4) applying a first thin coat of the natural nail polish onto the plurality of nails, after the natural nail polish is mixed well; (5) applying a second thin coat of the natural nail polish onto the plurality of nails, after the first coat is completely dried; (6) softening the applied natural nail polish by directly soaking the plurality of nails in a warm or hot water; and (7) removing the applied natural nail polish from the plurality of nails by lifting or pulling the applied natural nail polish.

12. The method of applying and removing the natural nail polish as claimed in claim 11, wherein there is about 30 seconds to about 3 minutes between the first thin coat and the second thin coat, wherein the first thin coat is dried; wherein the second thin coat is waterproof after about 30 minutes to about one hour; and wherein the applied natural nail polish is soaked about 30 seconds to 5 minutes in the warm or hot water for removal.

* * * * *